(12) United States Patent
Serra et al.

(10) Patent No.: US 7,291,176 B2
(45) Date of Patent: Nov. 6, 2007

(54) SYSTEM FOR ESTABLISHING THE ORIENTATION OF A MODULAR IMPLANT

(75) Inventors: Michael A. Serra, Cameron Park, CA (US); Shaun B. Hanson, Phoenixville, PA (US); Alfred S. Despres, Shingle Springs, CA (US); Robert German, Davis, CA (US)

(73) Assignee: Hayes Medical, Inc., Eldorado Hills, CA (US)

( * ) Notice: Subject to any disclaimer, the term of this patent is extended or adjusted under 35 U.S.C. 154(b) by 241 days.

(21) Appl. No.: 10/435,000

(22) Filed: May 9, 2003

(65) Prior Publication Data

US 2004/0059340 A1 Mar. 25, 2004

Related U.S. Application Data

(60) Provisional application No. 60/378,984, filed on May 9, 2002.

(51) Int. Cl.
*A61F 2/32* (2006.01)
(52) U.S. Cl. ............... 623/22.12; 623/22.42; 606/53; 606/87; 606/99; 606/102
(58) Field of Classification Search ............. 623/22.12, 623/22.42, 23.35; 606/87, 102, 53, 99
See application file for complete search history.

(56) References Cited

U.S. PATENT DOCUMENTS

| 5,800,556 | A | | 9/1998 | Sanders et al. |
|---|---|---|---|---|
| 5,860,969 | A | * | 1/1999 | White et al. ............. 623/23.35 |
| 5,906,644 | A | | 5/1999 | Powell |
| 5,951,564 | A | * | 9/1999 | Schroder et al. ............ 606/100 |
| 5,976,147 | A | | 11/1999 | LaSalle et al. |
| 6,063,091 | A | | 5/2000 | Lombardo et al. |
| 6,277,123 | B1 | * | 8/2001 | Maroney et al. ............ 606/102 |
| 6,330,845 | B1 | * | 12/2001 | Meulink ....................... 81/462 |
| 6,361,506 | B1 | | 3/2002 | Saenger et al. |
| 6,746,487 | B2 | * | 6/2004 | Scifert et al. ............ 623/22.12 |
| 2004/0122437 | A1 | * | 6/2004 | Dwyer et al. .................. 606/87 |
| 2004/0267372 | A1 | * | 12/2004 | Vanasse et al. .......... 623/22.11 |

* cited by examiner

*Primary Examiner*—Corrine McDermott
*Assistant Examiner*—Javier G. Blanco
(74) *Attorney, Agent, or Firm*—Pandisco & Pandisco

(57) ABSTRACT

This invention provides apparatus and a method for assembling a modular hip implant where the desired orientation of the neck component is uniquely determined during the trialing phase of the operation, and that same desired orientation is accurately reproduced during the implantation phase of the actual hip implant device.

7 Claims, 6 Drawing Sheets

SYSTEM FOR ESTABLISHING THE ORIENTATION OF A MODULAR IMPLANT

REFERENCE TO PENDING PRIOR PATENT APPLICATION

This patent application claims benefit of prior U.S. Provisional Patent Application Ser. No. 60/378,984 now abandoned, filed May 9, 2002 by Michael A. Serra et al. for METHOD FOR ESTABLISHING THE ORIENTATION OF MODULAR IMPLANTS, which patent application is hereby incorporated herein by reference.

FIELD OF THE INVENTION

This invention relates to medical apparatus and procedures in general, and more particularly to medical apparatus and procedures relating to total hip joints.

BACKGROUND OF THE INVENTION

The aim of Total Hip Arthroplasty ("THA") is the reduction of pain by restoring the form and function of a hip joint damaged by either trauma or disease. This is accomplished using engineered materials to construct an implantable device for the restoration of the joint mechanics and geometry, whereby the affected tissue is removed and replaced by the implantable device. Successful outcomes depend largely on the proper sizing, placement and orientation of the implant. Incorrect biomechanics (e.g., joint reaction forces, soft tissue balancing, leg length, etc.) can slow or prevent healing, cause gait abnormalities, result in dislocation of the joint, and lead directly to early implant failure, among other things.

The restoration of proper joint mechanics depends largely on good surgical technique, implants which are anatomically matched to the needs of the patient, and effective instrumentation for bony preparation, size and shape determination, and insertion of the final implant construct.

Prior to insertion of the actual implant, it is generally desirable to use a mock implant or "trial" as a means of evaluating the correct size and positioning of the implant within the bony canal. The surgeon implants the trial, reduces the joint and evaluates the stability of the joint, leg length discrepancies, and range of motion ("ROM"). This process of "trialing" is often iterative as the surgeon tries different trial implants until the satisfactory joint mechanics are achieved.

The stability and range of motion of the hip joint is achieved by placing the prosthetic femoral head in an orientation with respect to the proximal end of the femur (i.e., the "proximal femur") and knee joint that allows for a normal range of motion without impingement of the hip onto the acetabulum. This impingement can be either prosthetic or bony impingement. The tension of the joint, which provides stability, is achieved by adjusting the neck length of the implant. Neck length can be adjusted both vertically and horizontally, and is the distance between the center of the prosthetic head (i.e., the center of the acetabulum) and the centerline (or long axis) of the proximal femur. Increasing neck length increases the tension of the tendons and muscles that attach the proximal femur to the pelvis. The angular orientation of the neck of the femur with respect to the plane of the posterior condyles of the knee is defined as anatomic anteversion (FIG. 1).

The normal proximal femur has a gradual anterior twist to it so that the orientation of the endosteal envelope (i.e., inner bone geometry) gradually rotates externally (i.e., the head moves anteriorly relative to the transverse plane) in the proximal third of the femur until it culminates in the position of the femoral head. Thus the head of the femur is usually slightly more anteverted than the body of the femur with respect to the axis of the posterior condyles of the knee. The normal range of anteversion is about 20 degrees to about 30 degrees. However, various conditions can cause the natural anteversion to range from between about −20 degrees to about 50 degrees. When replacing the hip joint, the surgeon may need to change the patient's natural anteversion considerably so as to create proper and stable biomechanics of the hip joint.

Hip implants generally comprise four regions or sections: the head, the neck, the body, and the stem. The head section is almost always modular (i.e., detachable from the remainder of the implant). Most implants are one solid piece that comprises the neck, body, and stem regions. These one-piece hip implants are positioned inside the proximal femur in the orientation that best fits the body of the implant to the inside of the proximal femur (i.e., metaphysis). The neck of these devices either follows the orientation of the body exactly or is offset from the body by some fixed angle. Thus the neck of the device can be in only one orientation and the surgeon cannot change it to suit the particular anatomy of the patient. In many patients, this fixed orientation is sub-optimal and occasionally even insufficient, producing impingement or instability.

Modular implants can allow independent rotational positioning of the neck with respect to the body in the transverse plane, thereby providing the surgeon with the ability to solve the angular positioning issues of hip replacement surgery. Several types of these modular implants exist. However, with all currently available devices, the surgeon must visually estimate the correct orientation of the implant neck during the trial phase of the surgery. Anatomic landmarks such as the orientation of the proximal femur are most often used to gage anteversion. The surgeon essentially "eyeballs" the anteversion angle relative to the partially visible proximal femur. However, the surgeon has no idea what the actual mechanical anteversion angle is relative to the proximal femur. Often the surgeon makes a mark on the adjacent tissue to indicate the approximate orientation of the trial neck relative to the trial body. If the orientation of the trial neck and body thereafter has to be changed, the surgeon iteratively rotates the neck by some approximated angular amount to another position, until the leg mechanics seem correct. After the trial process is completed, the surgeon selects the appropriate implant components and inserts them into the bone. The surgeon must once again estimate the orientation of the neck relative to the body, hoping to achieve the same position that was achieved with the trial. This process often results in the surgeon settling for a "that looks about right" orientation.

No current instrument or method allows the surgeon to actually measure the anteversion of the prosthetic neck with respect to some reference frame.

No current instrument or method allows the surgeon to insert the implant neck into precisely the same orientation as was chosen in the trial step.

SUMMARY OF THE INVENTION

This invention provides apparatus and a method for assembling a modular hip implant where the desired orientation of the neck component is uniquely determined during the trialing phase of the operation, and that same desired orientation is accurately reproduced during the implantation phase of the actual hip implant device.

In one form of the present invention, there is provided a method for establishing the orientation of a modular hip implant neck, the method comprising: recording the orientation of the trial neck relative to a reference that is fixed in relationship with the femur; and inserting the modular neck component into the femur in the precise orientation that was determined by the recording step using the fixed reference.

In another form of the present invention, there is provided a method for establishing the orientation of a modular hip implant neck, the method comprising: determining the orientation of the trial implant neck relative to the knee joint and using that measurement to determine the initial orientation for the trial neck; recording the orientation of the trial neck relative to a reference that is fixed in relationship with the femur; and inserting the modular implant neck component into the femur in the precise orientation that was determined by the recording step using the fixed reference.

In another form of the present invention, there is provided an instrument for measuring the angular orientation of a trial neck with respect to a reference that is fixed with respect to the femur, the instrument comprising: a first member having a feature for engaging a portion of the trial neck to register its rotational position; a second member, coaxial to the first member, having a feature for engaging the fixed reference; and a recording mechanism for recording the position of the first member relative to the second member.

In another form of the present invention, there is provided an instrument for measuring the angular orientation of a modular hip implant neck portion with respect to a fixed reference, the instrument comprising; a first member having a feature for engaging a portion of the implant neck to register its rotational position; a second member, coaxial to the first member, having a feature for engaging the fixed reference; and a scale feature for showing the position of the first member relative to the second member.

In another form of the present invention, there is provided an instrument for measuring the angular orientation of a modular hip implant neck portion with respect to a fixed reference, the instrument comprising: a single member having a feature for engaging a portion of the implant neck to register its rotational position, and a scale feature for direct comparison to the fixed reference.

In another form of the invention, there is provided an instrument for measuring the relative angular orientation between two components of a modular hip, the instrument comprising: a single member having a feature for engaging a portion of the modular implant neck and having a scale feature oriented to allow direct observation of the angular orientation of the body.

BRIEF DESCRIPTION OF THE DRAWINGS

These and other objects and features of the present invention will be more fully disclosed or rendered obvious by the following detailed description of the preferred embodiments of the invention, which is to be considered together with the accompanying drawings wherein like numbers refer to like parts, and further wherein.

BRIEF DESCRIPTION OF THE PREFERRED EMBODIMENTS

This invention provides a novel method and apparatus for implanting a modular hip prosthesis, where the modular hip prosthesis has the ability to rotationally orient the neck. The method comprises uniquely determining the orientation of the trial neck component with respect to a reference that is fixed with respect to the femur. The fixed reference could be the implant body, an anatomic landmark (e.g., anatomic landmark 5) or an external reference. The fixed reference may comprise several features, a feature being an aspect or part of the reference that can be used to indicate the orientation of the overall feature. By way of example, the fixed reference can be the prepared body (i.e., a cavity prepared in the bone for the implant body 8) orientation. This may be formed by instruments prior to the trialing step. During the trialing step, the trial body registers on the reference and assumes the same orientation. The trial body has several features that may be used to indicate the orientation. These may be slots or holes in the trial body placed there expressly for indicating the orientation or may be geometric or compositional features of the trial body such as the most medial point on the trial, the tip of some section, a corner, edge, or point that exists primarily for some other purpose. Different features of the fixed reference can be used during each step to register the orientation. The orientation can be determined numerically or simply recorded by a mechanical device. The mechanical recording can be accomplished by having two components that register on features that simply lock together and record the orientation. Preferably, the numerical orientation of the neck with respect to the posterior condyles of the knee should also be able to be determined.

Thereafter, the prosthetic neck is implanted into the patient in precisely the same orientation, relative to the implant body, as was determined during the trial phase of surgery. This can be accomplished by either preassembling the neck to the body in the predetermined orientation prior to implant insertion into the proximal femur, or by fixing the neck to the body in the measured location once the body is implanted in the femur.

DETERMINING THE ORIENTATION OF THE TRIAL NECK

Figure 1:
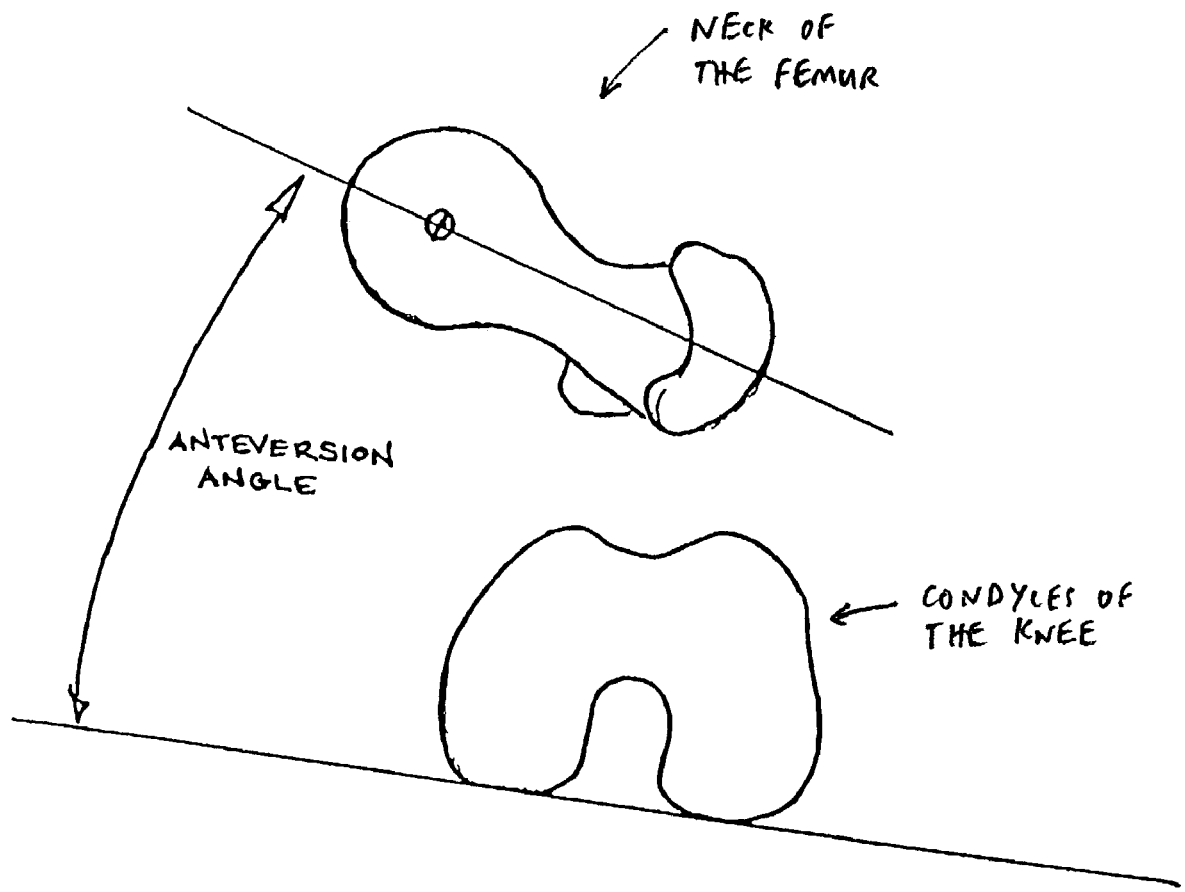
FIG. 1 is a schematic view illustrating the anteversion angle of a patient.
Figure 1A:
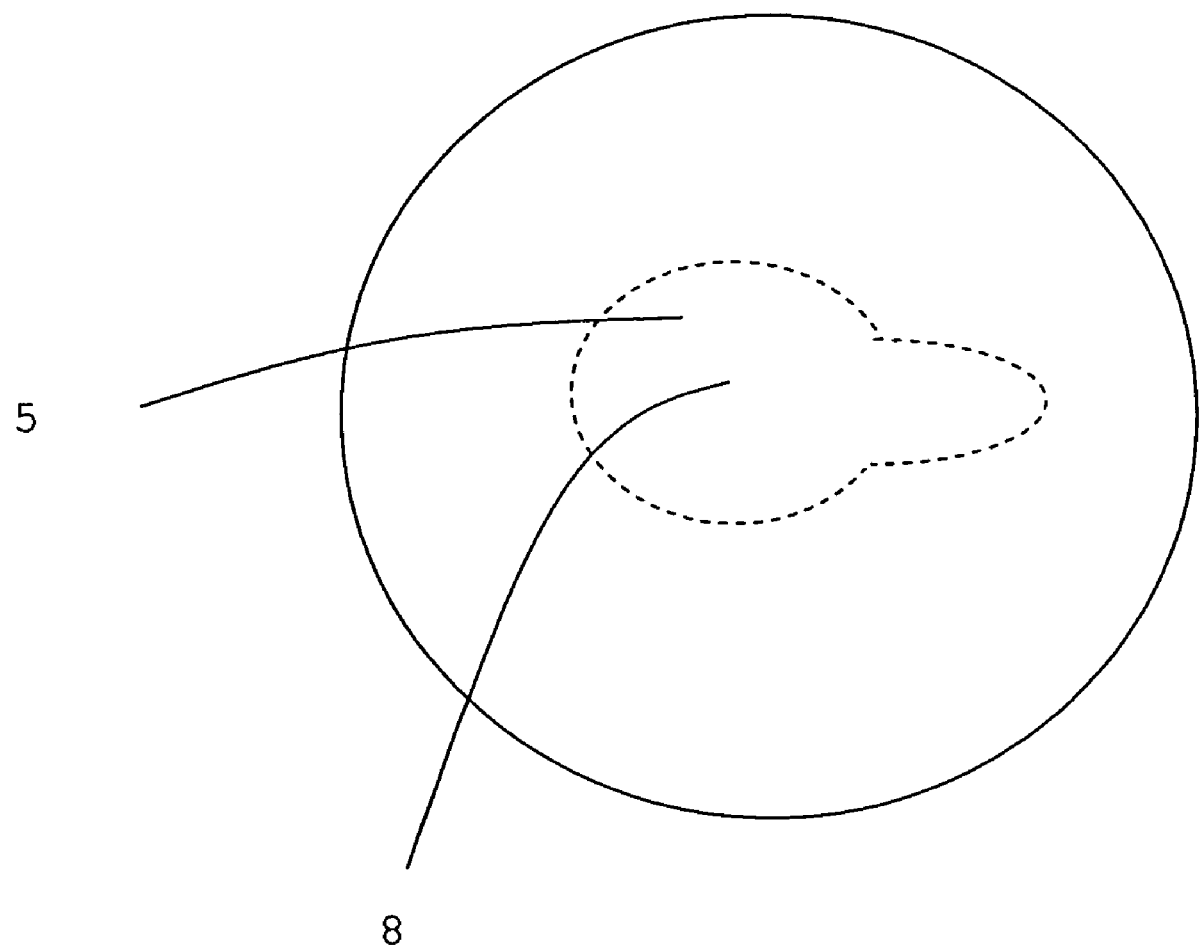
FIG. 1A is a top view illustrating a portion of the femur.
Figure 2:
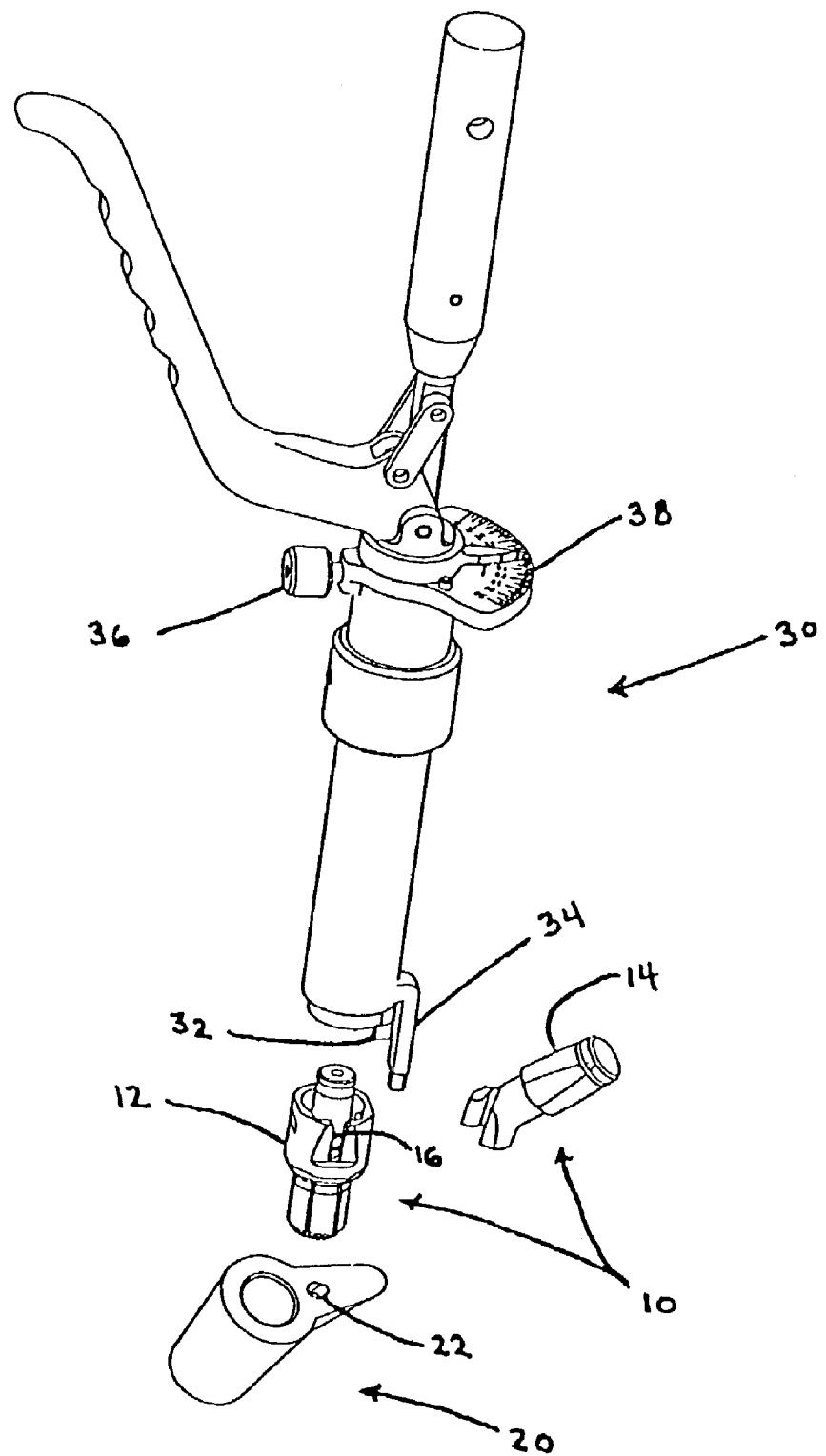
FIG. 2 is a schematic view illustrating apparatus for determining the orientation of the trial neck.

The trial neck 10 (FIG. 2) can be initially placed by eye into the trial body 20. The trial neck can be a one-piece element or can comprise two parts, the first part 12 determining the angular orientation and the second part 14 determining the horizontal and vertical offset.

In one embodiment, the trial body 20 is the fixed reference mentioned above. This is the most accurate when the modular implant body can be placed in the same location in the femur as was the trial body 20. A location feature 22 on the trial body 20, and a location feature 16 on the trial neck 10, are referenced by an instrument 30 so as to determine the rotational orientation of the two parts. In the embodiment shown in FIG. 2, the body reference 22 is located by instrument extension 34 and the neck reference 16 is located by instrument tab 32.

In one preferred form of the invention, body reference 22 is an opening in body 20 and instrument extension 34 is a finger for insertion into opening 22.

And in one preferred form of the invention, neck reference 16 is a slot in neck 10 and instrument tab 32 is a finger for insertion into slot 16.

It is preferable that the orientation of the neck 10 and body 20 be recorded or locked into the instrument 30 for later reference, such as by a set screw 36. It is also preferable that the instrument 30 provide a numerical orientation value, such as by a scale 38. If changes need to be made to the anteversion of the trial neck, they can be made in discrete, planned amounts, not just by some random or estimated increment.

It is also preferable that an instrument be provided to measure the orientation of the neck with respect to the posterior condyles of the knee. This can be accomplished by flexing the knee and using the tibia to indicate the direction perpendicular to the posterior condylar axis. A rod (not shown) securely aligned with the neck axis can be compared to the long axis of the flexed tibia, and the angle between the posterior condylar axis and the axis of the neck can be measured, changed, and set. This enables the surgeon to know the anatomic anteversion of the neck relative to the posterior condylar axis, and further allows the surgeon to set the angle of the neck relative to the body. Using this approach the surgeon can set the "implant" anteversion angle (i.e., the axis of the neck relative to the axis of the body), or the surgeon can set the "anatomic" anteversion angle (the axis of the neck relative to the posterior condylar axis).

IMPLANTATION

Figure 3:
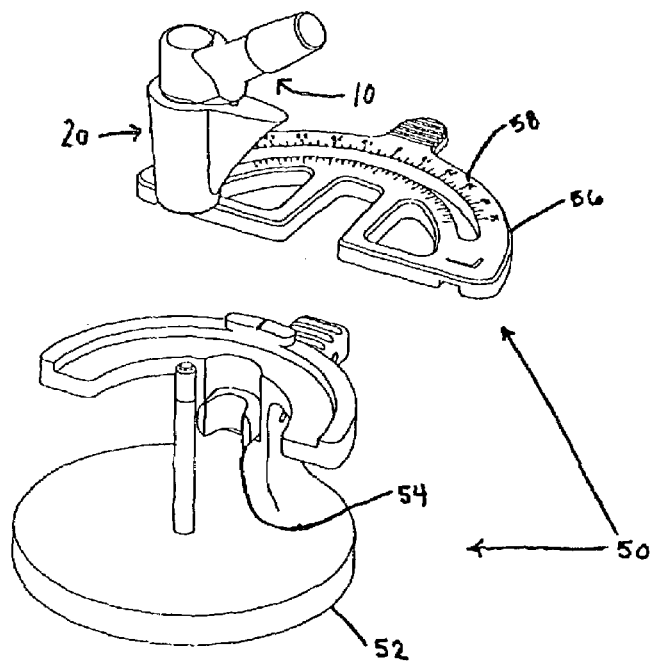
FIG. 3 is a schematic view illustrating apparatus for orienting the implant body and neck into the same orientation as the trial.
Figure 4:
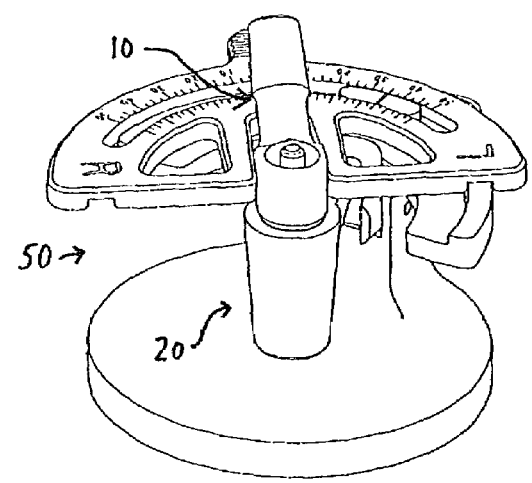
FIG. 4 is a schematic view illustrating the apparatus of FIG. 3 being used to orient the implant body and neck into the same orientation as the trial.

Once the desired orientation of the trial neck has been determined, the surgeon proceeds to assemble and insert the actual implant components. In the embodiment where the body of the implant is the reference, the neck and body components can be preassembled into the desired orientation before implantation. This may be accomplished with an orientation instrument 50 (FIG. 3) that can orient the implant body and neck into the same orientation as the trial. The reference features on the implant neck and body do not have to be the same as the trial neck and body, so long as they are properly related to one another so as to produce an equivalent result. The orientation instrument 50 of FIG. 3 has a base 52 and a retractable fork feature 54 that orients the body. The implant neck is placed in the body and a faceplate 56 is attached to the neck. The faceplate 56 is attached to the neck. The faceplate 56 has graduations 58 that match the graduations on scale 38 of the trial measuring instrument 30. The neck and faceplate are rotated so that the trial orientation reading is replicated (FIG. 4). The implant neck and body are then assembled in this position, and then the implant is implanted into the patient.

Figure 5:
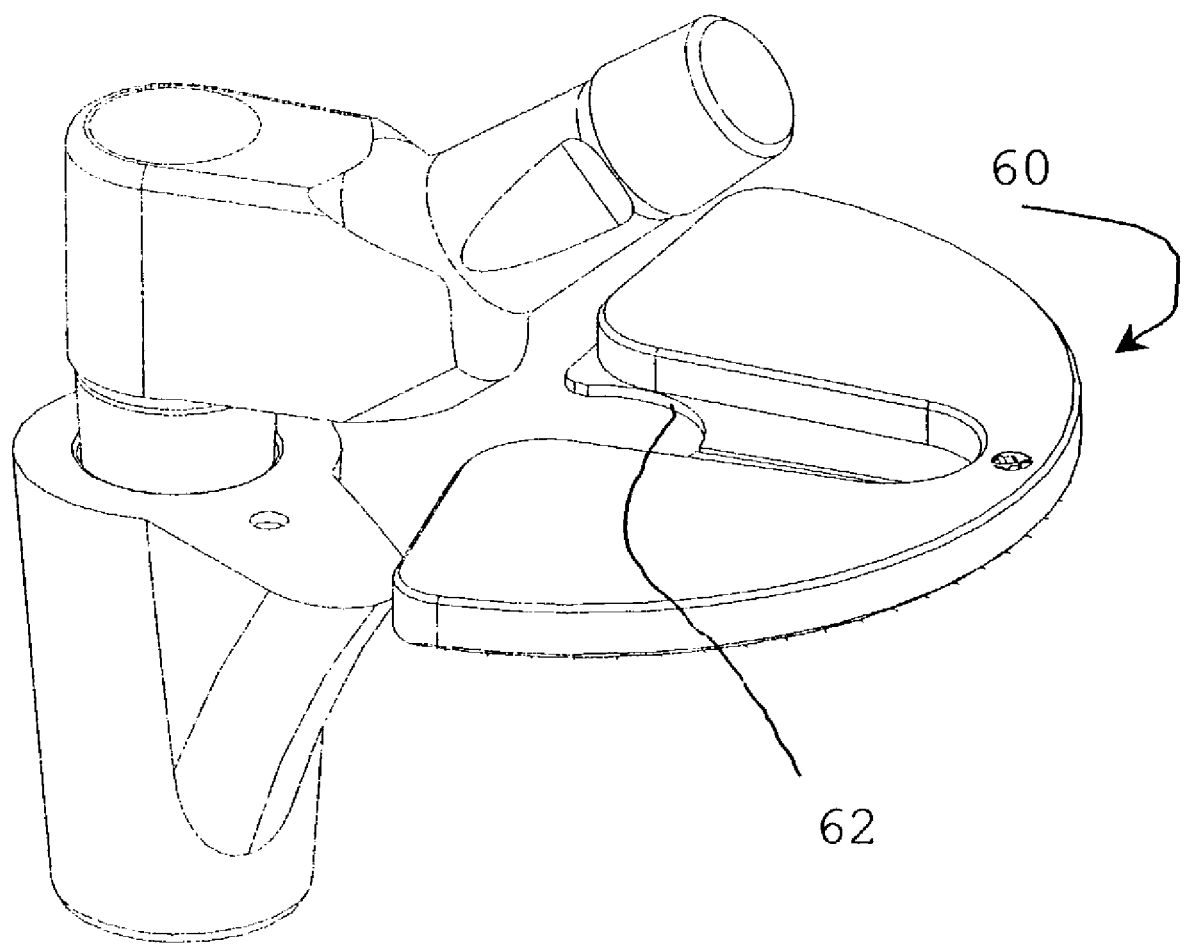
FIG. 5 is a schematic view illustrating an alternate apparatus for orienting the implant body and neck into the same orientation as the trial.
Figure 6:
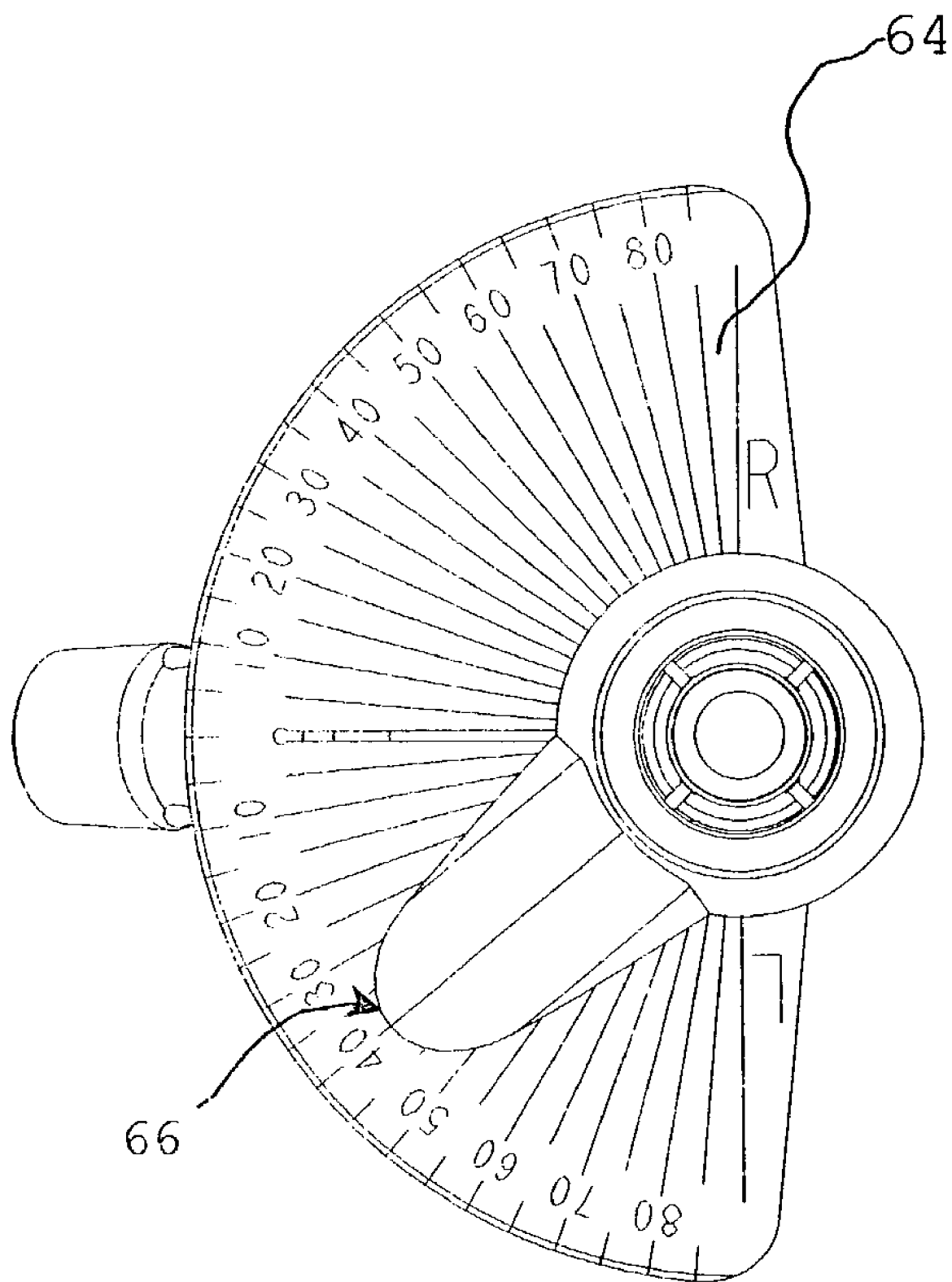
FIG. 6 is a bottom view illustrating the apparatus of FIG. 5 being used to orient the implant body and neck into the same orientation as the trial

Another embodiment of the orientation instrument is shown in FIG. 5. The instrument consists of a single piece 60 that engages a portion of the neck. It is preferable that the instrument have a feature allowing secure or "hands free" attachment to the neck 62. It is preferable that the instrument provide a numerical orientation value such as a scale 64. It is preferable that the scale be oriented in such a way as to provide a direct observation of the implant body such as the medial tip 66 (FIG. 6). It is also preferable that the instrument be constructed of translucent material to allow top down observation of the scale and medial tip.

In the case where the implant neck angle is set relative to the long axis of the tibia (indicating the axis of the posterior condyles), the angle of the trial neck relative to the trial body is measured and then recreated for the implanted neck and body.

In alternate embodiments, other reference features and locations can be used.

MODIFICATIONS

Still other embodiments of the present invention will be apparent to those skilled in the art in view of the present disclosure, and are considered to be within the scope of the present invention.

What is claimed is:

1. A method for determining and recording the orientation of a modular hip implant neck, the method comprising:
   providing an assembly comprising:
      a trial implant comprising:
         a trial body having (i) a bore and (ii) an opening for attachment to a recording instrument; and
         a trial neck having (i) a shaft which is adapted for insertion into the bore of the trial body and (ii) a portion for attachment to the recording instrument; and
      the recording instrument comprises an elongated body having a distal end and a proximal end, wherein the proximal end comprises (i) a first member for attachment to the trial neck and (ii) a second member coaxial with the first member for attachment to the trial body;
   adjusting the trial neck relative to the trial body so as to assume a desired orientation between the trial neck and the trial body, wherein the desired orientation is determined by orienting the trial neck in relation to a first anatomical reference and orienting the trial body in relation to a second anatomical reference;
   attaching the first member to the trial neck and the second member to the trial body so as to record the orientation of the trial neck and the trial body;
   providing a modular hip implant comprising a neck component and a body component;
   assembling the neck component and the body component in the recorded orientation; and
   inserting the assembled modular implant into a patient's femur.

2. The method of claim 1 wherein the recording of the orientation of the trial neck comprises making a mechanical recording of the orientation.

3. The method of claim 1 wherein one of the anatomical references is a cavity prepared in the femur for the assembled modular implant.

4. The method of claim 1 wherein one of the anatomical references is an anatomic landmark on the femur.

5. The method of claim 1 wherein one of the anatomical references is a knee joint.

6. The method of claim 1 wherein one of the anatomical references is the posterior condyle of a patient's knee.

7. The method of claim 1 wherein one of the anatomical references is a long axis of a patient's tibia.

* * * * *